United States Patent
Nakatani et al.

(10) Patent No.: US 9,310,325 B2
(45) Date of Patent: Apr. 12, 2016

(54) FOCUSED ION BEAM APPARATUS AND METHOD OF WORKING SAMPLE USING THE SAME

(71) Applicant: HITACHI HIGH-TECH SCIENCE CORPORATION, Minato-ku, Tokyo (JP)

(72) Inventors: Ikuko Nakatani, Tokyo (JP); Makoto Sato, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days.

(21) Appl. No.: 14/221,611

(22) Filed: Mar. 21, 2014

(65) Prior Publication Data
US 2014/0291512 A1  Oct. 2, 2014

(30) Foreign Application Priority Data

Mar. 27, 2013  (JP) .................. 2013-067320
Mar. 12, 2014  (JP) .................. 2014-048446

(51) Int. Cl.
*G01N 23/225*  (2006.01)
*H01J 37/304*  (2006.01)
*H01J 37/305*  (2006.01)
*G01N 1/32*  (2006.01)

(52) U.S. Cl.
CPC ........ *G01N 23/2258* (2013.01); *G01N 23/2251* (2013.01); *H01J 37/3045* (2013.01); *H01J 37/3056* (2013.01); *G01N 1/32* (2013.01); *H01J 2237/31745* (2013.01)

(58) Field of Classification Search
USPC ................................. 250/307, 310
See application file for complete search history.

(56) References Cited

U.S. PATENT DOCUMENTS

| 5,641,715 | A * | 6/1997 | Okamoto | G03F 7/0045 148/DIG. 137 |
| 8,442,300 | B2 * | 5/2013 | Tsuneta et al. | 382/145 |
| 9,136,089 | B2 * | 9/2015 | Wang | H01J 37/222 |
| 2007/0274593 | A1 * | 11/2007 | Tsuneta | G06T 7/0004 382/192 |
| 2011/0210248 | A1 * | 9/2011 | Hirose et al. | 250/310 |

FOREIGN PATENT DOCUMENTS

| JP | 03166744 | 7/1991 |
| JP | 09274879 | 10/1997 |
| JP | 2000100360 | 4/2000 |

* cited by examiner

*Primary Examiner* — Phillip A Johnston
*Assistant Examiner* — Hsien Tsai
(74) *Attorney, Agent, or Firm* — Adams & Wilks

(57) ABSTRACT

A focused ion beam apparatus includes an image generation unit that generates a sample image including location detection marks formed on a sample based on secondary charged particles generated from the sample by emission of a focused ion beam to the sample, and a display that which displays a sample image. A control unit which, in a case of performing working by emitting the focused ion beam to a working region of the sample that is beyond a display range, moves a sample stage, detects locations of the location detection marks included in the sample image after the movement of the sample stage as reference marks from the location detection marks included in the sample image before moving the sample stage, and controls an emission location of the focused ion beam based on the reference marks detected in the sample image after movement of the sample stage to correct a working location shift due to movement of the sample stage.

19 Claims, 9 Drawing Sheets

FOCUSED ION BEAM APPARATUS AND METHOD OF WORKING SAMPLE USING THE SAME

This application claims priority from Japanese Patent Application No. 2013-067320 filed on Mar. 27, 2013 and Japanese Patent Application No. 2014-048446 filed on Mar. 12, 2014, the entire subject-matters of which are incorporated herein by reference.

BACKGROUND

1. Technical Field

The disclosure relates to a focused ion beam apparatus which performs working of a sample with a focused ion beam, a method of working a sample using the apparatus, and a computer program for focused ion beam working.

2. Description of Related Art

In the related art, a focused ion beam (FIB) apparatus has been used for performing etching working of a semiconductor device, for example, to obtain a cross section for observation, or for making a sample as a thin piece to manufacture a sample piece for a transmission electron microscope (refer to, for example, Japanese Patent No. 2973211). In addition, in recent years, it is also necessary to perform working of a sample into various shapes using the focused ion beam apparatus.

However, if the working time becomes longer, a stage or the like for placing a sample thereon during the working of the sample may drift or a beam may be deflected by charging of the sample, and accordingly a working location of the sample may be shifted. Herein, there is a known technology of previously registering a location of a location detection mark formed on the sample before the working and adjusting an emission location of an ion beam so as to correct the shift between a mark location during the working and the location of the location detection mark before the working (refer to, for example, JP-A-9-274879).

If the ion beam is emitted to the location detection mark several times during the working to detect the location thereof, the mark may be damaged by an ion sputtering phenomenon and accordingly, the mark may not be recognized. Herein, there is a known technology of forming a plurality of location detection marks on a sample, previously registering a location of each mark before the working, and sequentially switching the mark to be used in location correction during the working (refer to, for example, JP-A-2000-100360).

SUMMARY

A working region of a sample is set using a sample image displayed on a display, and an ion beam is scanned two-dimensionally with a pixel of the sample image as a minimum unit of a size of a pixel to be irradiated with the ion beam, to perform image display and working of the sample. Herein, a ratio (W/D) of a width W showing a field of view (FOV) of the sample image on the display to a width D of the pixel to be irradiated with the ion beam on the sample is set as a "working magnification". Since the width W is normally constant due to limitation of the number of pixels of the display, as the working magnification increases (as D becomes smaller), working accuracy increases. However, since the width D does not become smaller than a spot diameter of the ion beam in practice, there is a limit of a maximum magnification of the working magnification. In addition, the working magnification is different from a "display magnification" which represents the size of the sample displayed on the display with respect to the size of the actual sample.

Accordingly, in a case where the working region of the sample is wide, when there is an intention of performing the working by displaying all of the working regions in the sample image, the working magnification becomes a low magnification, and the working accuracy may also be decreased. In contrast, if there is an intention of improving the working accuracy by setting the working magnification as a high magnification, since it is difficult to display all of the working regions in the sample image, it is necessary to perform the working while moving a sample stage and sequentially displaying the working regions in the image.

However, a positioning accuracy of physical (mechanical) movement of the sample stage is lower than a positioning accuracy of the ion beam emission, and an error of approximately several μm occurs. Accordingly, although the location detection mark of the sample image before the movement of the sample stage is detected to correct the location shift, new location shift occurs due to the movement of the sample stage, but since the original location detection mark is shielded by the switching of the sample image, it is difficult to correct the working location shift after the movement of the sample stage.

Therefore, illustrative aspects of the invention provide a focused ion beam apparatus capable of correcting working location shift even in a case of performing working of a working region which is beyond a display range of a sample image due to movement of a sample stage, a method of working a sample using the apparatus, and a computer program for focused ion beam working.

According to one illustrative aspect of the invention, there may be provided a focused ion beam apparatus comprising: a sample stage, which is configured to place a sample that is a working target thereon, and which comprises a movement mechanism configured to move a location of the sample; a focused ion beam emission mechanism configured to emit a focused ion beam to the sample; a detector configured to detect secondary charged particles generated with the emission of the focused ion beam to the sample; an image generation unit configured to generate a sample image including location detection marks formed on the sample, based on detection data of the detector; a display unit configured to display the sample image; and a control unit which, in a case of moving the sample stage and performing working by emitting the focused ion beam to a working region that is beyond a display range of the display unit, is configured to: detect a location of any location detection marks included in the sample image after the movement of the sample stage as a reference mark, from the location detection marks included in the sample image before the movement of the sample stage; detect a location of the reference mark in the sample image after the movement of the sample stage; and control an emission location of the focused ion beam based on the reference mark.

According to this focused ion beam apparatus, even in a case of moving the sample stage to perform the working of the working region beyond the display range of the sample image, after performing the working on the sample image with high magnification for increasing working accuracy, it is possible to perform working of the entire working region with high accuracy, while correcting the working location shift, using the reference mark included in the sample image after the movement of the sample stage.

According to another illustrative aspect of the invention, the control unit may be configured to detect the reference mark that is the closest to a movement destination of the sample stage.

According thereto, it is possible to reliably include the reference mark on the sample image after the movement of the sample stage.

According to still another illustrative aspect of the invention, the control unit may be configured to previously set the entire working region, and the control unit may be configured to set a movement distance of the sample stage, based on the entire working region which has been previously set and a width W representing a display size of the sample image displayed on the display unit.

According to this focused ion beam apparatus, it is possible to automatically perform the movement of the sample stage and the detection and the working of the reference mark after the movement, by previously setting the entire working region, on the sample image with low magnification.

According to still another illustrative aspect of the invention, the control unit may be configured to: set a movement distance of the sample stage; and detect the location of the reference mark on the sample image before the movement, based on the movement distance.

According to this focused ion beam apparatus, even in a case where it is necessary to move the sample stage in an ex-post manner to perform the working of a portion beyond the display range of the sample image, after performing working of only the working region in the sample image with high magnification for increasing the working accuracy, it is possible to correct the working location shift by the reference mark.

According to still another illustrative aspect of the invention, the control unit may be configured to form the reference mark based on the movement distance.

According to this focused ion beam apparatus, it is possible to form the location detection mark by determining the movement distance, without previously forming the location detection marks.

According to still another illustrative aspect of the invention, after performing the working in the sample image after the movement of the sample stage, the control unit may be configured to: set a new working area in the sample stage; form a new location detection mark at a location different from that of the reference mark in the sample image; extract each of feature amounts from the sample images before and after the forming of the location detection mark; and control an emission location of the focused ion beam to be emitted to the new working area so as to correct a location shift between the feature amounts.

According to this focused ion beam apparatus, since new location detection marks are formed in a sample image including a new working area, it is possible to accurately perform working of the working area using the new location detection marks, although the known reference mark is damaged by the emission of the ion beam.

Incidentally, a drift may occur during the formation of the new location detection marks, and the location of the location detection marks may be shifted. Herein, it is possible to accurately perform the working of the location of the original working area, by correcting the location shift using each feature amount extracted from the sample image before and after forming the location detection marks, as references of the location, and therefore it is possible to perform the working with higher accuracy.

According to still another illustrative aspect of the invention, there may be provided a method of working a sample using a focused ion beam apparatus, the method comprising: generating a sample image including location detection marks formed on a sample, based on secondary charged particles generated with emission of a focused ion beam to the sample which is a working target; displaying the sample image; moving a sample stage which the sample is placed thereon; in a case of performing working by emitting the focused ion beam to a working region which is beyond a display range of the displayed sample image, detecting a location of any location detection marks included in the sample image after the movement of the sample stage as a reference mark, from the location detection marks included in the sample image before the movement of the sample stage; detecting a location of the reference mark in the sample image after the movement of the sample stage; and controlling an emission location of the focused ion beam based on the reference mark.

According to still another illustrative aspect of the invention, there may be provided a non-transitory computer-readable medium having a computer program for focused ion beam working stored thereon and readable by a computer, the computer program, when executed by the computer, causes the computer to perform operations comprising: an image generation process comprising generating a sample image including location detection marks formed on a sample, based on secondary charged particles generated with emission of a focused ion beam to the sample which is a working target; displaying the sample image; moving a sample stage which the sample is placed thereon; in a case of performing working by emitting the focused ion beam to a working region which is beyond a display range of the displayed sample image: detecting a location of any location detection marks included in the sample image after the movement of the sample stage as a reference mark, from the location detection marks included in the sample image before the movement of the sample stage; detecting a location of the reference mark in the sample image after the movement of the sample stage; and controlling an emission location of the focused ion beam based on the reference mark.

According to the illustrative aspects of the present invention, it is possible to correct the working location shift using the focused ion beam apparatus, even in a case of moving the sample stage to perform the working of the working region beyond the display range of the sample image.

BRIEF DESCRIPTION OF THE DRAWINGS

FIGS. 8A and 8B are diagrams in which, FIG. 8A shows a target location of new location detection marks formed in a sample image, and FIG. 8B shows location shift of location detection marks due to drift.

DETAILED DESCRIPTION

Hereinafter, illustrative embodiments of the present invention will be described with reference to the drawings.

Figure 1:
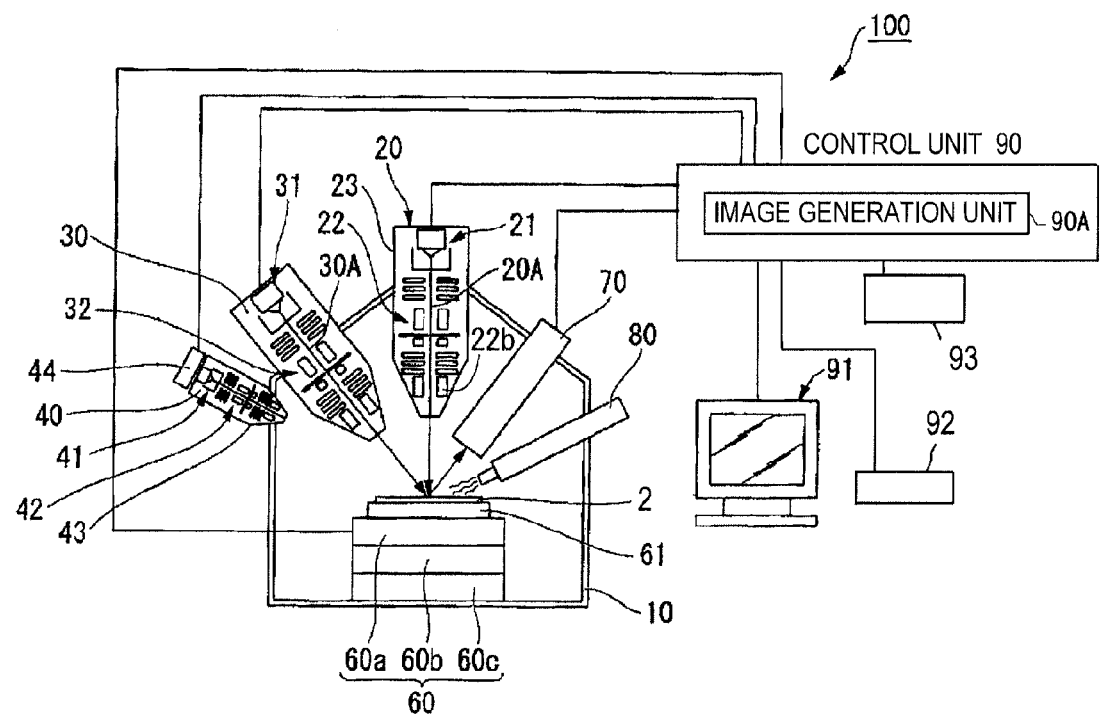
FIG. 1 is a block diagram showing an entire configuration of a focused ion beam apparatus according to illustrative embodiments of the present invention.

FIG. 1 is a block diagram showing an entire configuration of a focused ion beam apparatus 100 according to illustrative embodiments of the present invention. In FIG. 1, the focused ion beam apparatus 100 includes a vacuum chamber 10, an ion beam emission system ("focused ion beam emission mechanism" in claims) 20, an electron beam emission system 30, an argon ion beam emission system 40, a sample stage 60, a secondary charged particle detector ("detector" in claims) 70, a gas gun 80, and a control unit 90. An internal pressure of the vacuum chamber 10 is reduced to a predetermined degree of vacuum, and a part or all of component parts of the focused ion beam apparatus 100 are disposed in the vacuum chamber 10.

The sample stage 60 movably supports a sample base 61, and a sample 2 is placed on the sample base 61. The sample stage 60 includes a movement mechanism which can displace the sample base 61 with five axes. This movement mechanism includes an XYZ movement mechanism 60b which moves the sample base 61 along an X axis and a Y axis which are parallel to a horizontal plane and orthogonal to each other and a Z axis which is orthogonal to the X axis and the Y axis, a rotation mechanism 60c which rotates the sample base 61 around the Z axis, and a tilt mechanism 60a which rotates the sample base 61 around the X axis (or Y axis). The sample stage 60 moves the sample 2 to an emission location of an ion beam 20A by displacing the sample base 61 with the five axes.

The control unit 90 can be configured with a computer including a CPU as a central processing unit, a storage unit (RAM and ROM) 93 which stores data, programs, and the like, and an input port and an output port which perform input and output of signals between the computer and an external device. In the control unit 90, the CPU executes various processes based on programs stored in the storage unit 93, and controls each component part of the focused ion beam apparatus 100. The control unit 90 is electrically connected to control wires of the ion beam (hereinafter, the focused ion beam is appropriately abbreviated as the "ion beam") emission system 20, the electron beam emission system 30, the argon ion beam emission system 40, the secondary charged particle detector 70, and the sample stage 60.

The control unit 90 includes an image generation unit 90A.

The control unit 90 is configured to drive the sample stage 60 based on a command of software or input of an operator, and adjust an emission location or an emission angle of the ion beam 20A to a surface of the sample 2 by adjusting a location or a posture of the sample 2.

Incidentally, an input unit 92 such as a keyboard which acquires input indications of an operator is connected to the control unit 90.

The image generation unit 90A generates image data representing a sample surface by converting secondary charged particles detected by the secondary charged particle detector 70 into a luminance signal, and generates a sample image based on this image data. The sample image is configured to be output to a display device (display, or "display unit" in claims) 91 connected to the control unit 90 and to designate a working region, which will be described later, on the display device 91.

This working region is stored in the storage unit 93 as image data (bitmap data).

The control unit 90 detects locations of location detection marks included in the sample image if necessary, and records the locations of the location detection marks before the working in the storage unit 93 as initial locations. The control unit 90 controls an ion source 21 and an ion beam emission system optical system 12 to control the emission of the ion beam 20A. In detail, the control unit 90 controls the output of the ion beam 20A emitted from the ion source 11, and controls a deflector 22b to control a width D (see FIG. 2) of the ion beam 20A. The control unit 90 controls the deflector 22b so as to adjust the emission location of the ion beam 20A without moving the sample stage 60 and perform the working with the width D along the working region. Further, the control unit 90 compares the initial locations of the location detection marks stored in the storage unit 93 and the location of the location detection marks during the working, and controls the deflector 22b so as to correct shift between both locations, to adjust the emission location of the ion beam 20A, and compensate location shift at the time of the working (working location shift). Further, the control unit 90 also can cause the ion beam 20A to be emitted to form the location detection marks at predetermined locations of the suitable sample.

An operator designates a location (coordinates) of the working region of the sample on the sample image, and designation information is transmitted to the control unit 90 through the input unit 92. The control unit 90 registers the received location in the storage unit 93.

The ion beam emission system 20 includes the ion source 21 which generates ions, and an ion optical system 22 which forms ions flowing out from the ion source 21 in a focused ion beam and scans the ions. The ion beam 20A which is a charged particle beam is emitted to the sample 2 on the sample stage 60 in the vacuum chamber 10, from the ion beam emission system 20 including an ion beam lens barrel 23. At that time, secondary charged particles such as secondary ions or secondary electrons are generated from the sample 2. The secondary charged particles are detected by the secondary charged particle detector 70 to acquire an image of the sample 2. Further, the ion beam emission system 20 performs etching working of the sample 2 in the emission range by increasing irradiance of the ion beam 20A.

The ion optical system 22 is configured to include, for example, a condenser lens for focusing the ion beam 20A, an aperture for adjusting the focus of the ion beam 20A, an aligner for adjusting an optical axis of the ion beam 20A, an objective lens for focusing the ion beam 20A with respect to the sample, and the deflector 22b which scans the ion beam 20A on the sample.

The electron beam emission system 30 includes an electron source 31 which emits electrons, and an electron optical system 32 which forms the electrons emitted from the electron source 31 into a beam shape and scans the electrons. By emitting an electron beam 30A emitted from the electron beam emission system 30 to the sample 2, secondary electrons are generated from the sample 2, but the generated secondary electrons can be detected by the secondary charged particle detector 70 to acquire the image of the sample 2. Herein, the electron beam 30A emitted from an electron beam lens barrel 33 is emitted to the location of the sample 2 which is the same location as that for the ion beam 20A.

The argon ion beam emission system 40 includes an argon ion source 41, an argon ion optical system 42, and an argon ion beam lens barrel 43, and further includes a beam location control unit 44 which controls an emission location of an argon ion beam. The argon ion beam for cleaning the sample 2 is emitted from the argon ion beam emission system 40.

The secondary charged particle detector 70 detects the secondary charged particles (secondary electrons or secondary ions) generated from the sample 2, when the ion beam 20A or the electron beam 30A is emitted to the sample 2.

The gas gun 80 releases a predetermined gas such as etching gas to the sample 2. By emitting the ion beam 20A to the sample 2 while supplying the etching gas from the gas gun 80, it is possible to increase an etching rate of the sample by the ion beam 20A. Further, by emitting the ion beam 20A to the sample 2 while supplying compound gas from the gas gun 80, it is possible to perform deposition of a local gas component in the vicinity of the emission region of the ion beam 20A.

Next, with reference to FIG. 2 to FIG. 4, in the focused ion beam apparatus according to the first illustrative embodiment of the present invention, a detection process of the location detection marks when moving the sample stage to perform the working of the sample will be described. In the first illustrative embodiment, it is assumed that, as shown in FIG. 3, after previously setting an entire working region 2W (point A to point C) with a sample image G3 with the working magnification as a low magnification P2 and previously forming location detection marks M1 and M2, the location detection marks are detected on sample images G1 and G2 with the working magnification as a high magnification P1 and the working of the sample is performed, as shown in FIG. 2.

As described above, the ratio (W/D) of the width W representing the field of view (FOV) of the sample image on the display unit 91 (display), and the width D of the pixel to be irradiated with the ion beam on the sample is set as the "working magnification".

Figure 2:
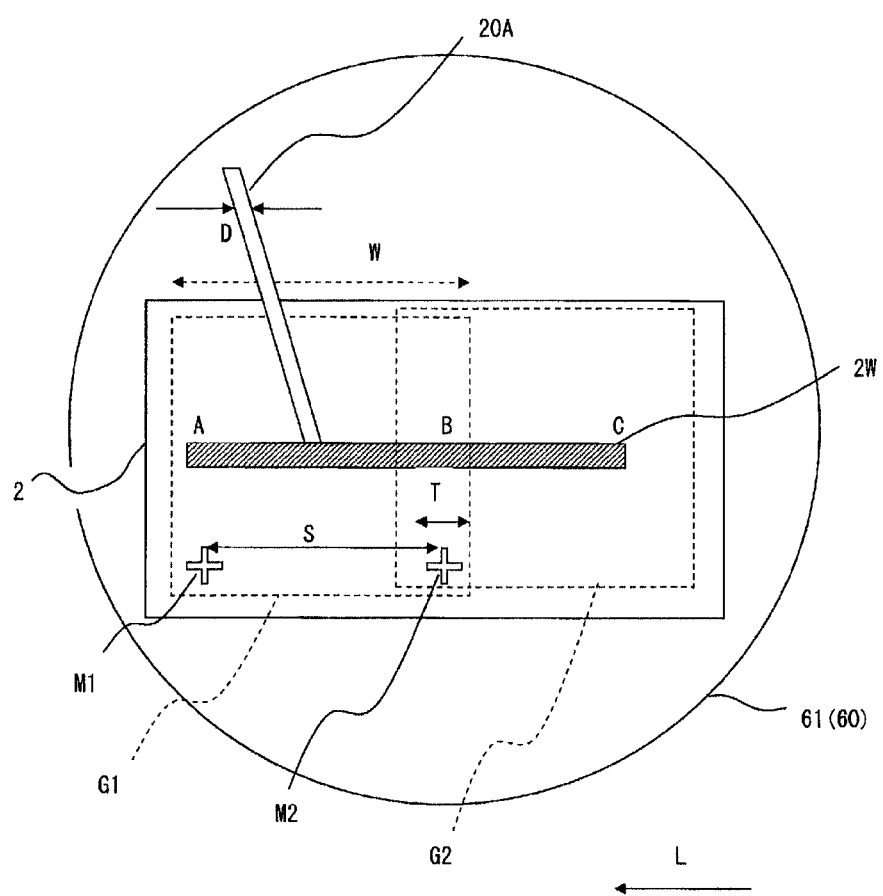
FIG. 2 is a diagram showing a detecting method of location detection marks when performing working of a sample by moving a sample stage in a first illustrative embodiment of the present invention.
Figure 3:
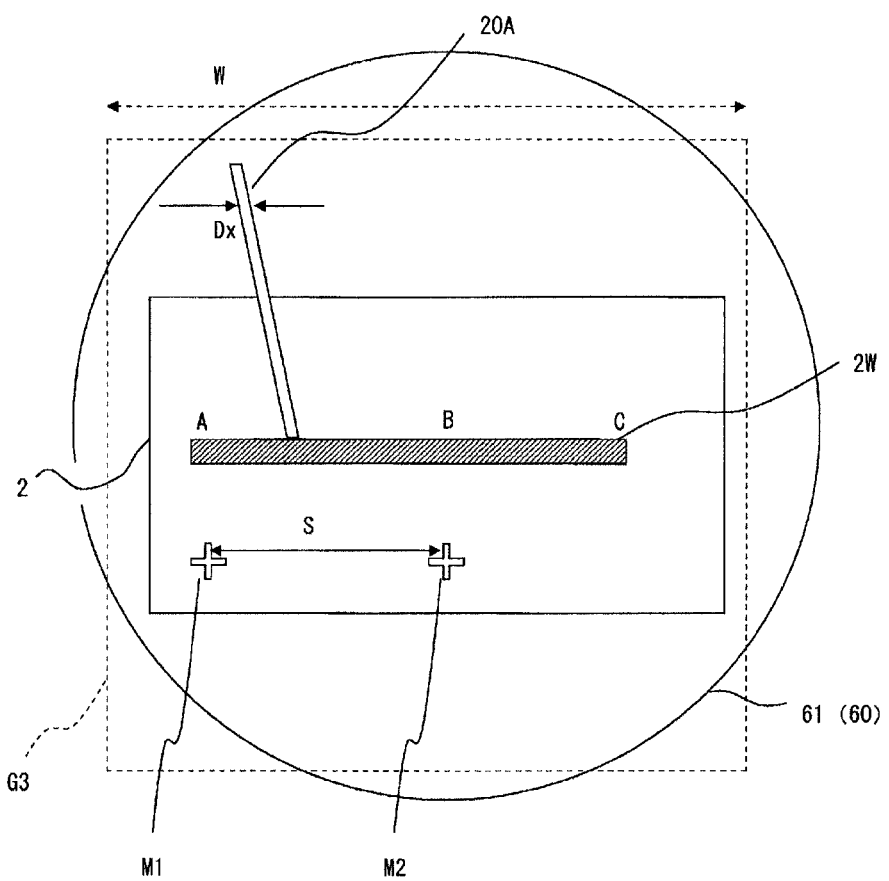
FIG. 3 is a diagram showing a method of previously providing a working region on a sample image with a low magnification and previously forming location detection marks in the first illustrative embodiment of the present invention.

FIG. 2 is a diagram showing the detection method of the location detection marks M1 and M2 when moving the sample stage 60 to perform the working of the sample 2. In FIG. 2, the sample 2 is placed on the sample base 61, and the sample stage 60 movably supports the sample base 61.

The working of the sample is performed using the sample images G1 and G2 and the width D is set to be small (to be equivalent to the spot diameter of the ion beam) in order to increase the working accuracy, and accordingly, a magnitude P1 is set to be (width W/width D of the ion beam 20A). Therefore, the working is performed in a state where the working region 2W stands out from the sample image G1.

As described above, since it is difficult to display the entire working region 2W in the sample image G1, after working a part (point A to point B) of the working region 2W in the sample image G1 with the ion beam 20A, the sample stage 60 is moved to the left by a movement distance L, and the rest of the working region 2W (point B to point C) is displayed in the sample image G2, and is subjected to the working with the ion beam 20A in the same manner as described above. For convenience, the sample images G1 and G2 are displayed at separate locations, but the sample stage 60 is moved to the left and the sample images G1 and G2 are superimposed at the same location, in practice.

Herein, in order to prevent a working location shift of each of the sample images G1 and G2, first, in the sample image G1, the working is performed while correcting the location shift based on the location detection mark M1 formed on a lower left end (point A side) of the sample 2. Next, the location of the location detection mark M2 of the sample image G1 on a lower right end (point B side) which is included in the sample image G1 before the movement of the sample stage 60 and is closest to a movement destination of the sample stage 60 (right side in FIG. 2 in an opposite direction to a movement direction of the sample stage 60) is detected. The location detection mark M2 is set as a reference mark. In the sample image G2 after the movement of the sample stage 60, the location of the location detection mark (reference mark) M2 is detected and the working is performed while correcting the location shift.

According thereto, it is possible to increase the working accuracy due to the magnification P1, and to perform the working of the entire working region 2W (point A to point C) while correcting the working location shift, even in a case where the sample stage 60 is moved.

The movement distance L is adjusted so as to display the location detection mark M2 in the sample image G2. It is necessary to set the movement distance L to be smaller than a value obtained by subtracting a distance T between the lower right end of the sample image G1 and the left end of the location detection mark M2 from the width W, so as to display the location detection mark M2 in both of the sample images G1 and G2. Incidentally, the shape of the location detection marks M1 and M2 is not limited to a cross shape shown in FIG. 2.

Next, with reference to FIG. 3, a method of previously setting the working region 2W (point A to point C) and previously forming the location detection marks M1 and M2 will be described. First, in order to display the entire working region 2W (point A to point C), the sample image G3 is displayed with the magnification P2 lower than the magnification P1. In the magnification P2, since a width Dx of the ion beam 20A is smaller than the width D in the magnification P1 and the working accuracy also decreases, acquisition of the sample image G3 by the ion beam 20A and setting of the working region 2W are performed without performing the working on the sample image G3 with the magnification P2.

The entire working region 2W (point A to point C) is set on the sample image G3. Further, the location detection marks M1 and M2 are formed at predetermined locations of the sample 2. Herein, it is necessary to set a space S between the location detection marks M1 and M2 along the movement direction to be smaller than the width W.

The formation locations of the location detection marks M1 and M2 may be arbitrarily determined on the sample image G3 by an operator, or may be automatically determined in the system based on the size of the working region 2W. In the latter case, the movement distance L which is smaller than the width W is set, based on the location (coordinates) of the working region 2W (point A to point C) along the movement direction and the width W of the sample image along the movement direction with the magnification P1, for example. Further, the movement distance L is set to be (W-T) by considering the value T described above. Incidentally, the value T, for example, may be previously determined as a default value, or in a case where the location detection mark M2 is formed at an arbitrary location by an operator, the value T may be calculated after detecting the location of the location detection mark M2 in the system.

According thereto, the working region 2W is set and the location detection marks M1 and M2 are appropriately formed, and then the working shown in FIG. 2 is performed. Incidentally, the formation of the location detection marks M1 and M2 may not be performed with the steps of FIG. 3, but may be performed on the sample image G1 shown in FIG. 2.

Next, with reference to FIG. 4, a flow of processes of FIG. 2 and FIG. 3 will be described. In the flow described below, the image generation unit 90A acquires detection data of the secondary charged particles from the secondary charged particle detector 70, generates the sample image which shows the surface shape of the sample 2, and transmits the sample image to the display device 91, and the display device 91 displays the sample image.

First, as shown in FIG. 3, an operator designates the location (coordinates) of the entire working region 2W (point A to point C) on the sample image G3 displayed with the magnification P2, and the designation information is transmitted to the control unit 90 through the input unit 92. The control unit 90 registers the received location in the storage unit 93, and sets the working region 2W (Step S2). Next, the control unit 90 calculates the locations of the location detection marks M1 and M2 with a predetermined space having a relationship of W>S with respect to the width W with the magnification P1, based on the coordinates of the working region 2W registered in the storage unit 93, and emits the ion beam 20A to the locations of the sample 2 to form the location detection marks M1 and M2 (Step S4). The formation locations of the location detection marks M1 and M2 may be arbitrarily determined on the sample image G3 by an operator. In this case, the control unit 90 forms the location detection marks at locations designated by an operator, instead of performing the process of Step S4.

Next, the control unit 90 detects the location detection mark M1 of the sample image G1 on the lower left end (point A side), on the sample image G1 with the magnification switched to the magnification P1 (Step S6), and corrects the working location shift (Step S8). In Step S6, first, the control unit 90 detects the location of the location detection mark M1 before the working to previously register the location in the storage unit 93. Then, the control unit 90 performs the detection of the location detection mark M1 if necessary in Step S6, even during the working. The control unit 90 adjusts the emission location of the ion beam 20A by the deflector 22b, so as to correct the shift between the mark location which is detected if necessary in Step S6 and the mark location which is initially registered.

Next, the control unit 90 performs the working of a part of the working region 2W (point A to point B) by the ion beam 20A without moving the sample stage 60, based on the coordinates of the working region 2W on the sample image G1 (Step S10).

Then, in Step S12, the control unit 90 determines whether or not the working in Step S10 has ended, and in a case of "No" in Step S10, the process returns to Step S6, and in a case of "Yes" in Step S10, the process ends and proceeds to Step S14. The determination of the end of the process in Step S10 is, for example, performed by confirming whether or not the emission location of the ion beam 20A reaches the right end (point B) of the working region 2W in the sample image G1.

Incidentally, in the detection of the location detection mark M1 in Step S6, the location detection mark M1 may be searched for in the image of the region (left side of FIG. 2) opposite to the movement destination (right side of FIG. 2) of the sample stage 60, in the sample image G1, for example, or all of the location detection marks M1 and M2 may be searched for from the sample image G1 and the mark M1 opposite to the movement destination (right side of FIG. 2) of the sample stage 60 may be extracted from the marks.

The process in Step S10 may be performed for each width D of the ion beam 20A, the detection process in Step S6 may be performed each time the process in Step S10 is performed (that is, each width D), and the detection process may be performed each time the working in Step S10 is performed several times. This is applied to the corresponding working and the detection process described below, in the same manner as described above.

Next, in Step S14, the control unit 90 detects the location detection mark (reference mark) M2 of the sample image G1 on the lower right end (point B side) and previously registers the location detection mark in the storage unit 93. As described above, in a case where all of the location detection marks M1 and M2 are searched for in Step S10 and the locations thereof are previously registered in the storage unit 93, Step S14 is not necessary.

Next, the control unit 90 sets the movement distance L of the sample stage 60 as described above, based on the coordinates registered in Step S2 and the width W, and moves the sample stage 60 to the left by the movement distance L (Step S16).

The movement indication of the sample stage 60 may be performed by an operator, and in this case, Step S16 is not necessary.

Next, the control unit 90 detects the reference mark M2 of the sample image G2 on the lower left end (point B side), on the sample image G2 after moving the sample stage 60 (Step S18), and corrects the working location shift (Step S20). In Step S18, the control unit 90 performs the detection of the reference mark M2 during the working, if necessary. Further, the control unit 90 adjusts the emission location of the ion beam 20A by the deflector 22b, so as to correct the shift between the mark location which is detected if necessary in Step S18 and the mark location which is registered in Step S14.

Next, the control unit 90 performs the working of the rest of the working region 2W (point B to point C) by the ion beam 20A without moving the sample stage 60, based on the coordinates of the working region 2W, on the sample image G2 (Step S22).

Figure 4:
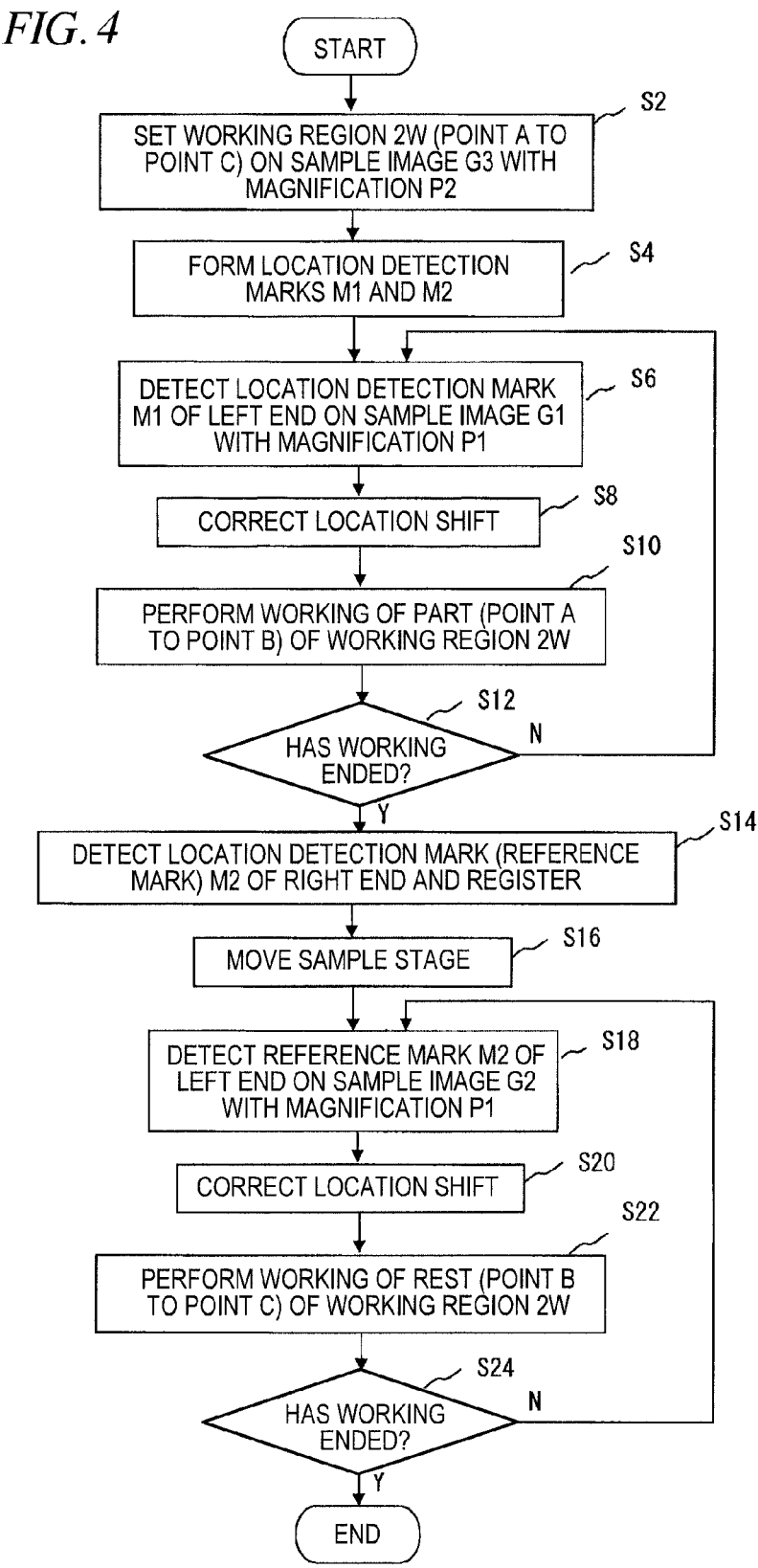
FIG. 4 is a diagram showing a flow of processes of FIG. 2 and FIG. 3.

Next, in Step S24, the control unit 90 determines whether or not the working in Step S22 has ended, and in a case of "No" in Step S24, the process returns to Step S18, and in a case of "Yes" in Step S24, the process of FIG. 4 ends. The determination of the end of the working in Step S22 is, for example, performed by confirming whether or not the emission location of the ion beam 20A reaches the right end (point C) of the working region 2W in the sample image G2.

Next, with reference to FIG. 5 and FIG. 6, in the focused ion beam apparatus according to a second illustrative embodiment of the present invention, a detection process of the location detection marks when moving the sample stage to perform the working of the sample will be described. In the second illustrative embodiment, it is assumed that, after performing the working of the sample on the sample image G1 with the high magnification P1 without previously setting the entire working region on the sample image with the low magnification, the sample stage 60 is moved in an ex-post manner and the working beyond the sample image G1 is performed.

Figure 5:
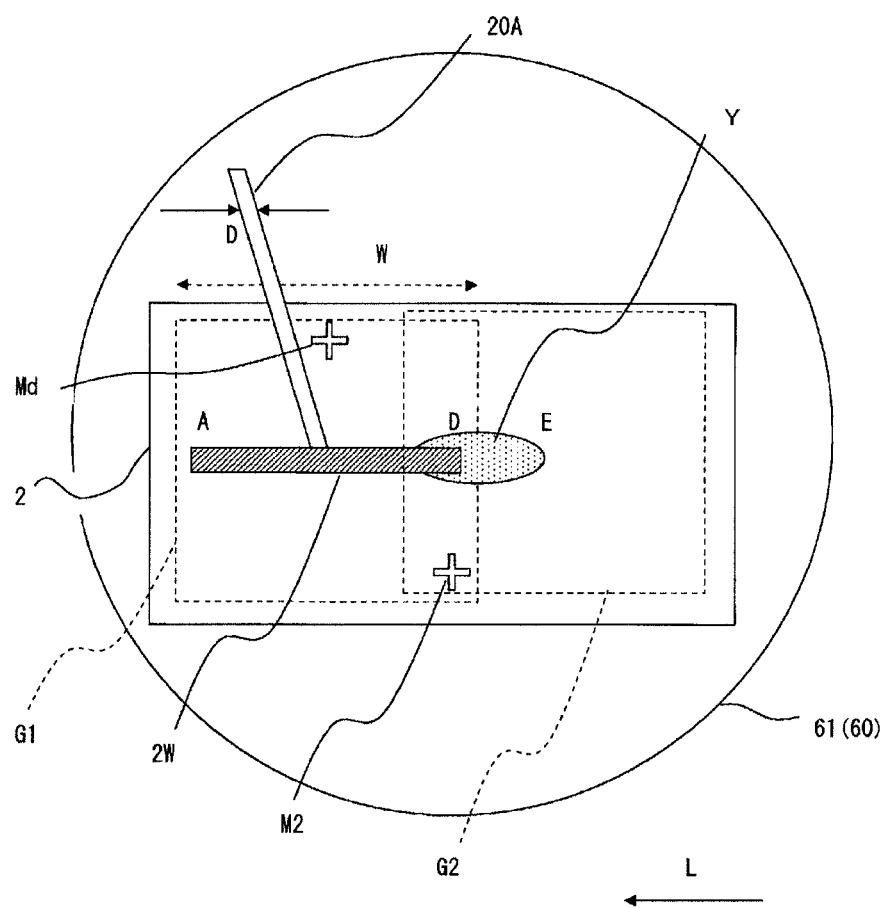
FIG. 5 is a diagram showing a method of performing working of a sample while moving a sample stage in a second illustrative embodiment of the present invention.

FIG. 5 is a diagram showing a case of moving the sample stage 60 to further perform the working of the right side with respect to the sample image G1, in order to remove entire impurity Y, since a part of the impurity Y is observed on the right end of the sample image G1 when the working region 2W (point A to point D) located in the sample image G1 is subjected to the working. For convenience, the sample images G1 and G2 are displayed at separate locations, but the sample stage 60 is moved to the left and the sample images G1 and G2 are superimposed at the same location, in practice.

The working of the working region 2W in the sample image G1 and the correction method of the location shift are the same as those in the first illustrative embodiment. However, in FIG. 5, a location detection mark Md is previously and automatically formed in an upper center portion of the sample 2 as a default location, and the location shift is corrected based on the location detection mark Md on the sample image G1.

After the working of the working region 2W is finished, when the movement of the sample stage 60 is set in order to remove the impurity Y, the location detection mark M2 is formed at a location (right end of the sample image G1 of FIG. 5) close to the movement destination of the sample stage 60 in the sample image G1.

After that, the sample stage 60 is moved to the left by the movement distance L, a (working region) of the impurity Y is displayed in the sample image G2, the correction of the location shift is performed using the location detection mark M2 in the sample image G2, and the working of the impurity Y is performed. The working and the correction method of the location shift are the same as those in the first illustrative embodiment.

According thereto, even in the case where the sample stage is moved in an ex-post manner after performing the working of one working region, it is possible to increase the working accuracy, and to perform the working of the entire working regions 2W and Y while correcting the working location shift.

Next, with reference to FIG. 6, a flow of the processes of FIG. 5 will be described.

First, as shown in FIG. 5, an operator designates the location (coordinates) of the entire working region 2W (point A to point D) on the sample image G1 displayed with the magnification P1, and the designation information is transmitted to the control unit 90 through the input unit 92. The control unit 90 registers the received location in the storage unit 93, and sets the working region 2W. Next, an emission control unit 90C forms the location detection mark Md at an appropriate default location on the sample image G1 (Step S104). In the example of FIG. 5, the location detection mark Md is automatically formed in the upper center portion of the sample 2 as a default location. The formation locations of the location detection mark Md may be arbitrarily determined on the sample image G1 by an operator. In this case, the emission control unit 90C forms the location detection marks at locations designated by an operator, instead of performing Step S104.

Next, the control unit 90 detects the location detection mark Md of the sample image G1 on the lower left end (point A side), on the sample image G1 (Step S106), and corrects the working location shift (Step S108). The processes in Steps S106 and S108 are the same as those in Steps S6 and S8 of FIG. 4, and therefore the descriptions thereof will be omitted.

The control unit 90 performs the working of the entire working region 2W (point A to point D) by the ion beam 20A without moving the sample stage 60, based on the coordinates of the working region 2W on the sample image G1 (Step S110).

Next, in Step S112, the control unit 90 determines whether or not the working in Step S110 has ended, and in a case of "No" in Step S110, the process returns to Step S106, and in a case of "Yes" in Step S110, the process ends and proceeds to Step S114.

Then, in Step S114, the control unit 90 determines presence and absence of movement setting of the sample stage 60. As described above, after finishing the working of the working region 2W, an operator inputs the movement distance L of the sample stage 60 through the input unit 92, in order to remove the impurity Y. This input information is registered in the storage unit 93 as the movement distance L by the control unit 90. Accordingly, the control unit 90 refers to the fact of whether or not the movement distance L is registered in the storage unit 93, and can determine the presence and absence of movement setting.

Figure 6:
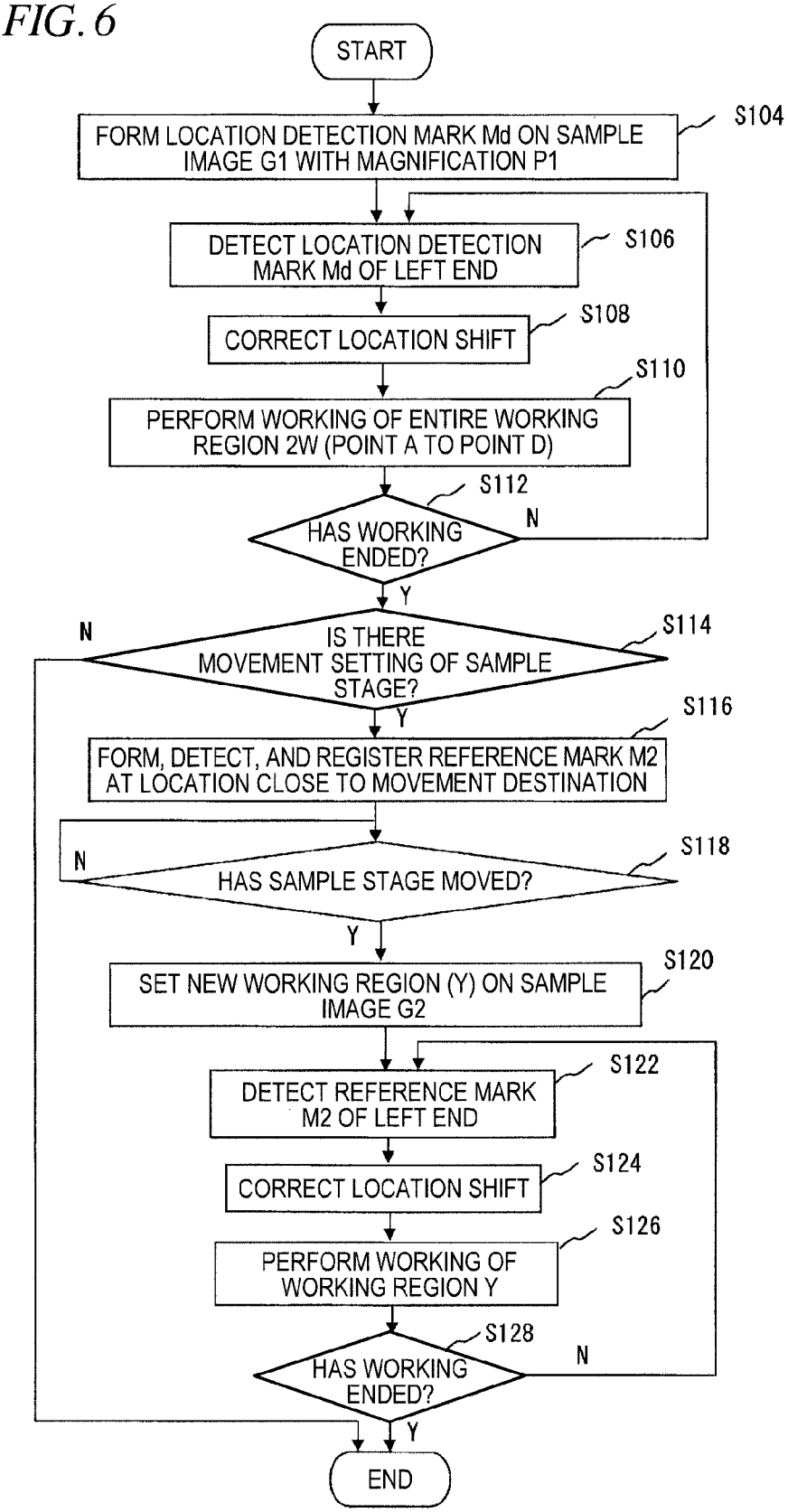
FIG. 6 is a diagram showing a flow of a process of FIG. 5.

In a case of "No" in Step S114, it is determined that there is no movement and all the working are finished, and accordingly the process of FIG. 6 ends. In a case of "Yes" in Step S114, the process proceeds to Step S116.

Next, in Step S116, the control unit 90 forms the location detection mark (reference mark) M2 at a predetermined location close to the movement destination (that is, the right end of the sample image G1), based on the movement distance L. The control unit 90 detects the reference mark M2 and previously registers the reference mark in the storage unit 93.

The formation indication of the reference mark M2 may be performed by an operator, and in this case, the forming process of the reference mark M2 in Step S116 is not necessary.

The location close to the movement destination may be previously determined. For example, if the movement destination is the right end side of the sample image G1, a location which is separated from the right end to the inside by a predetermined distance may be set. Further, in a case where this location is superimposed on the working region 2W, the location may be shifted so as not to be superimposed thereon. The control unit 90 may be configured to search for a mark of the set location.

Next, the control unit 90 determines whether or not the movement of the sample stage 60 has ended (Step S118), and in a case of "No" in Step S118, the process is on standby, and in a case of "Yes" in Step S118, the process proceeds to Step S120. The movement of the sample stage 60 is performed by the control unit 90 based on the movement distance L.

In Step S120, an operator designates a location (coordinates) of a new working region Y corresponding to the range of the impurity Y on the sample image G2 after the movement, and a working region setting unit 90D sets the working region Y, based on the designation information thereof.

Next, the control unit 90 detects the reference mark M2 of the sample image G2 on the lower left end (point D side) (Step S122), and corrects the working location shift (Step S124). In Step S122, the control unit 90 performs detection of the reference mark M2 if necessary, during the working. Further, the control unit 90 adjusts the emission location of the ion beam 20A by the deflector 22b, so as to correct the shift between the mark location which is detected if necessary in Step S124 and the mark location which is registered in Step S116.

Next, the control unit 90 performs the working of the working region Y by the ion beam 20A on the sample image G2, without moving the sample stage 60, based on the coordinates of the working region Y (Step S126).

Next, in Step S128, the control unit 90 determines whether or not the working in Step S126 has ended, and in a case of "No" in Step S128, the process returns to Step S122, and in a case of "Yes" in Step S128, the process of FIG. 6 ends. The determination of the end of the working in Step S126 is, for example, performed by confirming whether or not the emission location of the ion beam 20A reaches the right end of the working region Y in the sample image G2.

The present invention can be applied to a technology of repeatedly performing a cross section working which is so-called "cut-and-see" working, and observation.

Figure 7:
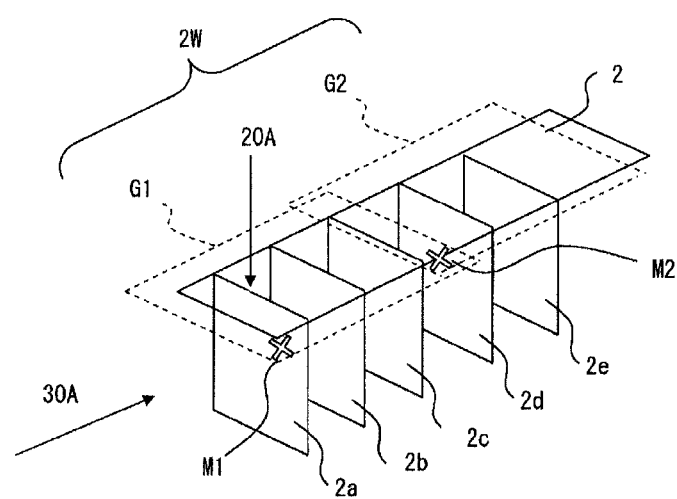
FIG. 7 is a diagram showing a method of performing working of a sample when the present invention is applied to a "cut-and-see" technology.

As shown in FIG. 7, in the "cut-and-see" working, the cross section working of the sample 2 by the ion beam 20A, and acquisition of a SEM image by emitting the electron beam 30A to cross sections 2a to 2e, are repeatedly performed. In detail, after moving the ion beam 20A in one direction and performing etching working of the sample 2 to form the cross section 2a, the SEM image (or a reflected electron image) of the cross section 2a is acquired. Then, the ion beam 20A is moved to the right in FIG. 7 to further perform the etching working of the sample 2, and the cross section 2b which is substantially parallel with the cross section 2a at a predetermined interval is formed on the right side of the cross section 2a. Then, the SEM image of the cross section 2b is acquired. Hereinafter, in the same manner as described above, the ion beam 20A is sequentially moved to the right direction, the cross sections 2c to 2e which are parallel with the cross section 2a are sequentially formed, and the SEM image of each cross section is acquired. Further, by combining the plurality of acquired SEM images of the cross sections with each other, a three-dimensional image inside the sample can be constructed.

Meanwhile, in the same manner as the process of FIG. 2, also in FIG. 7, the cross section working of the sample 2 by the ion beam 20A may be performed using the sample images G1 and G2, and the working may be performed with the high magnification P1 in order to increase the working accuracy. In this case as well, the working is performed in a state where the working region 2W (corresponding to the formation regions of the cross sections 2a to 2e) stands out from the sample image G 1. Accordingly, after a part (cross sections 2a to 2c) of the working region 2W is subjected to the working by the ion beam 20A in the sample image G1, the sample stage 60 is moved to the left, the rest of the working region 2W (cross sections 2c to 2e) is displayed in the sample image G2, and the working is performed by the ion beam 20A in the same manner as described above.

At this time, in the same manner as in the first illustrative embodiment, in order to prevent the working location shift of each of the sample images G1 and G2, first, the working is performed while correcting the location shift based on the location detection mark M1 formed on the sample image G1 and the location detection mark M2 formed on the sample image G2. Accordingly, it is possible to increase the working accuracy due to the magnification P1, and to perform the working of the entire working region 2W (cross sections 2a to 2e) while correcting the working location shift, even in a case where the sample stage 60 is moved.

However, as in "cut-and-see" working of FIG. 2, FIG. 5, or FIG. 7 described above, after moving a sample stage 60 to perform the working of a working area 2W (cross sections 2a to 2e), the working may be desired to be performed by setting a new working area Y in the sample image G2 (the case in which the working area Y is set in order to remove impurities, after performing the working of the working area 2W, corresponds to this, as shown in FIG. 5). Herein, the working area Y may be automatically set so as to extend the working area 2W.

Figure 8A:
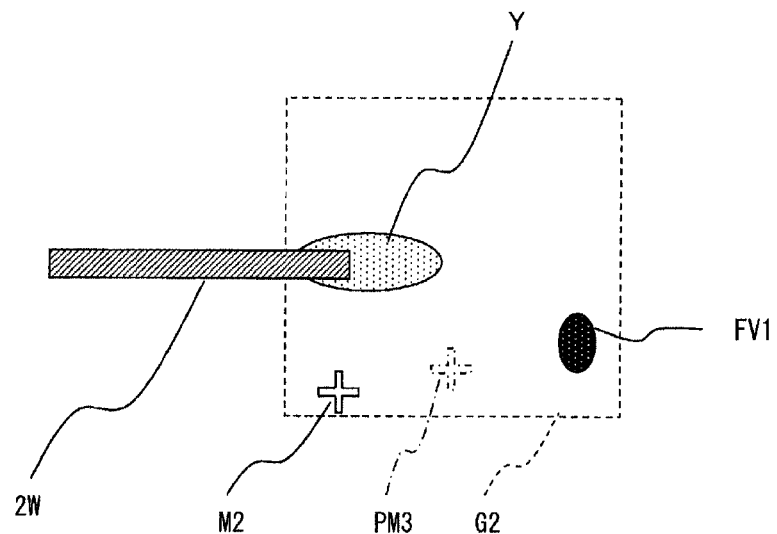

In this case, as shown in FIG. 8A, if a new location detection mark M3 (see FIG. 8B) is formed at a predetermined location PM3 which is different from a reference mark M2 in the sample image G2, and an emission location of an ion beam 20A to the working area Y is controlled based on this location detection mark M3, it is possible to accurately perform the working of the working area Y using the new location detection mark M3, although the reference mark M2 is damaged by the emission of the ion beam 20A.

Figure 8B:
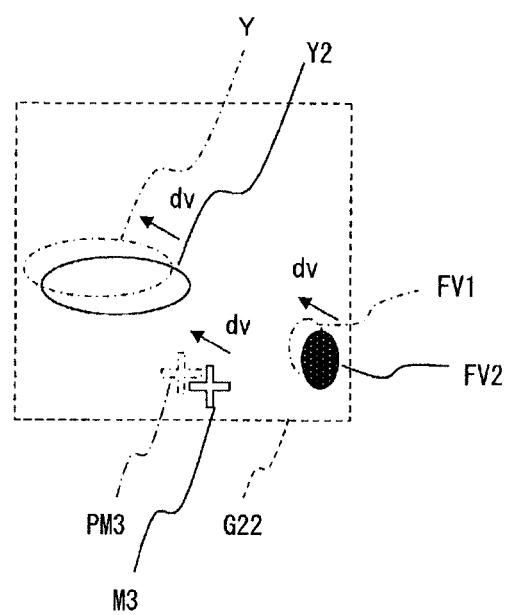

However, a drift may occur during the formation of the location detection mark M3 by the ion beam 20A, and as shown in FIG. 8B, the location detection mark M3 actually formed in the sample image G22 may be shifted by a shifted amount dv from the predetermined location PM3. In this case, since the original working area Y is positioned by a relationship with the predetermined location PM3, the location of the working area Y2 with the location detection mark M3 as a reference, may also be shifted from the original working area Y. Incidentally, the sample image after forming the actual location detection mark M3, is denoted as a "sample image G22" for differentiating from the sample image G2 before the formation of the location detection mark M3.

Herein, each of feature amounts FV1 and FV2 is extracted from the sample images G2 and G22, and the shifted amount dv is detected from the shift of the location of each of the feature amounts FV1 and FV2. Herein, the feature amounts FV1 and FV2 may have a feature pattern or shape in each of the sample images G2 and G22 excluding the location detection mark M3. For example, in a case where a structure having a pattern or feature exists in a sample surface, the feature amounts FV1 and FV2 can be set as the shape thereof, or can be set as the feature shape (worked groove or the like) of the working area 2W which is already subjected to the working. The feature amounts FV1 and FV2 can be extracted by using, for example, a well-known feature extraction algorithm of the image process (edge detection, corner detection, outline detection, region division, or the like).

Incidentally, when extracting the feature amounts FV1 and FV2, the image data of the entire sample images G2 and G22 may be acquired, or the image data of a part of the sample images G2 and G22 in the vicinity of the feature amounts FV1 and FV2 may be acquired. The shifted amount dv described above can be detected from a relative location relationship between the sample images G2 and G22 (or a part thereof), and the feature amounts FV1 and FV2.

Next, as shown in FIG. 8B, the location of the working area Y2 in the sample image G22 is corrected (location of the original working area Y is calculated), on the basis of the detected shifted amount dv. The ion beam 20A is emitted to the original working area Y with the corrected location, to perform the working. Accordingly, although the location of the location detection mark M3 is shifted due to the drift during the formation of the location detection mark M3 in the sample image G22, this shift can be corrected to accurately perform the working of the location of the original working area Y, and therefore it is possible to perform the working with higher accuracy.

Incidentally, after performing the working with the sample image G22, when moving the sample stage to perform the working in the next working area, the location detection mark M3 can be included in the sample image after the movement, to be used as the reference mark.

Accordingly, although the location of the location detection mark (reference mark) itself is shifted due to the drift, in each sample image after moving the sample stage, it is possible to correct the location shift of the working area due to the location shift of each reference mark, in the manner as described above, and it is possible to perform the working of the working area with higher accuracy.

Figure 9:
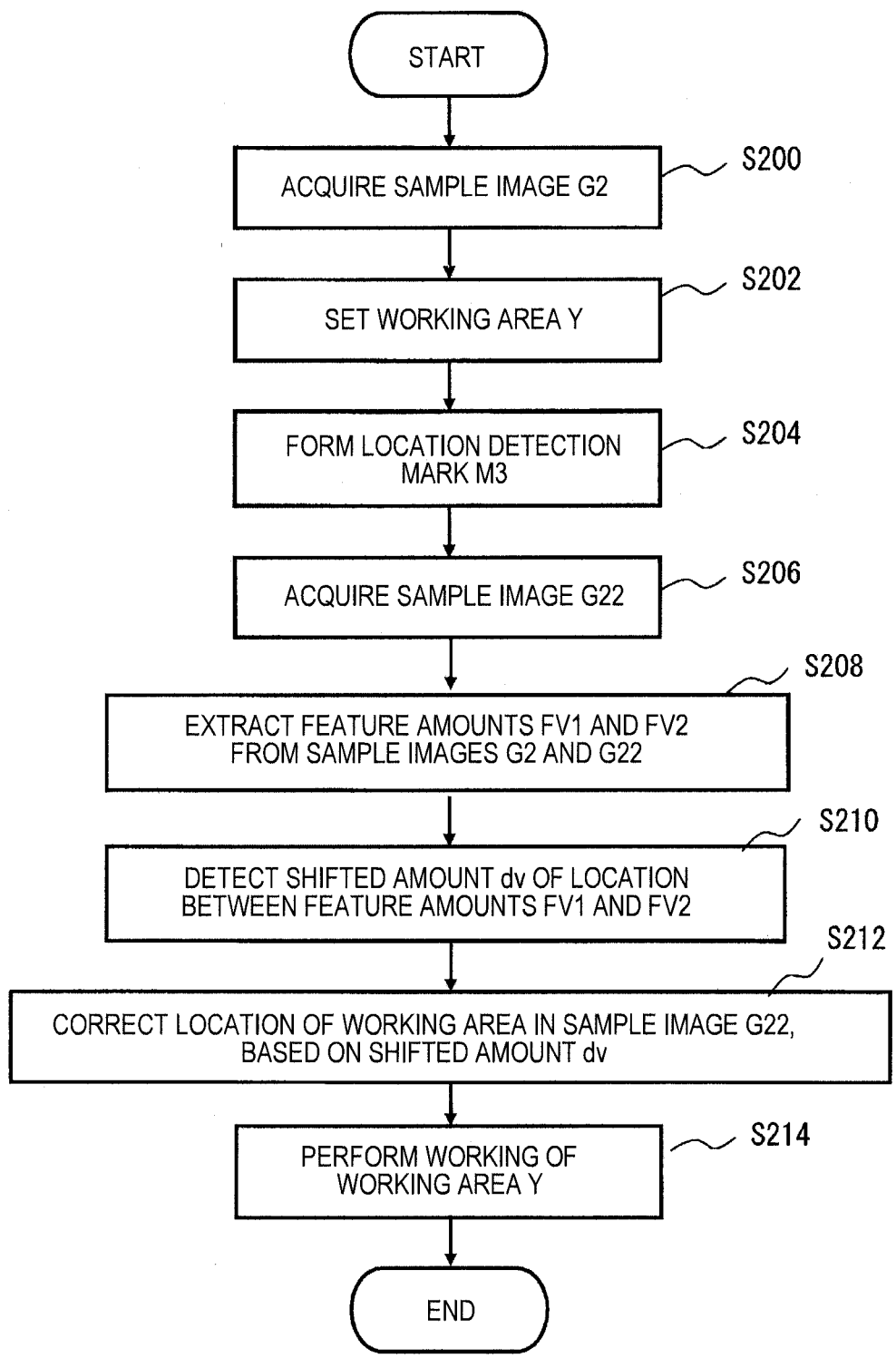
FIG. 9 is a diagram showing a flow of a process of FIG. 8.

Next, a flow of a process of FIG. 8 will be described with reference to FIG. 9.

First, a control unit 90 acquires the sample image G2 displayed with magnification P1 (Step S200). An operator designates the location (coordinates) of the new working area Y corresponding to a range of impurity Y on the sample image G2, and working area setting unit 90D sets the working area Y based on the designation information thereof (Step S202). Incidentally, Step S202 is the same as Step S120 of FIG. 6.

Next, emission control unit 90C forms the location detection mark M3 at a suitable default location (corresponding to the predetermined location PM3) on the sample image G2

(Step S204). Incidentally, the formation location (predetermined location PM3) of the location detection mark M3 may be arbitrarily determined by an operator on the sample image G2, and in this case, the emission control unit 90C forms the location detection mark M3 at the predetermined location PM3 designated by the operator, instead of performing the process in Step S204.

Next, the control unit 90 acquires the sample image G22 in which the location detection mark M3 is formed and which is displayed with the magnification P1 (Step S206).

Then, the control unit 90 extracts feature amounts FV1 and FV2 from the sample images G2 and G22 (Step S208). The control unit 90 detects the shifted amount dv from the shift of the locations of the feature amounts FV1 and FV2 (Step S210).

Further, in Step S212, the control unit 90 corrects the location of the working area Y2 in the sample image G22 (calculates the location of the original working area Y), based on the shifted amount dv. Then, the control unit 90 performs the working of the working area Y with the ion beam 20A, on the sample image G22, based on the coordinates of the original working area Y (Step S214).

The present invention is not limited to the illustrative embodiments described above, and various modifications and addition of equivalents included within the scope of the present invention can be performed.

For example, in the example of FIG. 2, the location detection mark M1 and the reference mark M2 which are detected for correcting the location shift during the working in the sample image G1 before the movement of the sample stage 60 are different from each other, but the same location detection mark may be detected before and after the movement. For example, in the example of FIG. 2, only the location detection mark M2 close to the movement destination may be formed without forming the location detection mark M1, and the location detection mark M2 may be detected in both the sample images G1 and G2. In the same manner as described above, in the example of FIG. 5, if the default formation location of the location detection mark Md is accidently a location corresponding to the location detection mark M2, the same location detection mark M2 is detected before and after the movement.

However, since the mark is damaged when the ion beam is emitted to the location detection mark several times during the working, it is preferable to set to detect different location detection marks in the sample images G1 and G2. Accordingly, the plurality of location detection marks may be previously formed on each of the sample images G1 and G2, registered in the storage unit 93, and managed so as to allow detection of different location detection marks on each of the sample images G1 and G2 and so that the marks to be detected in the sample images G1 and G2 are not superimposed on each other.

As the location detection mark M2 included in the sample image after the movement, a mark which is close to the movement destination among the location detection marks in the sample image G1 before the movement is preferable, and the mark which is closest thereto is more preferable. The distance between the location detection mark and the movement destination may be set as the distance with an image end closest to the movement destination in the sample image G1 before the movement.

Incidentally, in a case of moving the sample stage obliquely upward on the sample image G1, the sample 2 may be obliquely rotated and move transversely or longitudinally.

What is claimed is:

1. A focused ion beam apparatus comprising:
a sample stage, which is configured to place a sample that is a working target thereon, and which comprises a movement mechanism configured to move a location of the sample;
a focused ion beam emission mechanism configured to emit a focused ion beam to the sample;
a detector configured to detect secondary charged particles generated from the sample by the emission of the focused ion beam to the sample;
an image generation unit configured to generate a sample image including location detection marks formed on the sample, based on detection data of the detector;
a display unit configured to display the sample image; and
a control unit which, in a case of moving the sample stage and performing working by emitting the focused ion beam to a working region of the sample that is beyond a display range of the display unit, is configured to:
form location detection marks on at least one of the sample and the sample image on the display unit;
perform working of at least part of the working region of the sample by irradiating the sample with the ion beam on a first sample image while detecting a location of a first location detection mark formed at a processing starting point side and controlling an emission location of the focused ion beam based on the first location detection mark to correct a working location shift due to movement of the sample;
detect a location of any one of the location detection marks, which is to be included in a second sample image after the movement of the sample stage, as a reference mark, from the location detection marks included in the first sample image before the movement of the sample stage;
switch the sample image from the first sample image which includes a processed working region to the second sample image which includes an unprocessed working region by moving the sample stage;
perform working of the unprocessed working region by irradiating the sample with the ion beam on the second sample image while detecting a location of the reference mark in the sample image after the movement of the sample stage; and
control an emission location of the focused ion beam based on the reference mark to correct a working location shift due to movement of the sample stage.

2. The focused ion beam apparatus according to claim 1, wherein the control unit is configured to detect the reference mark that is the closest to a movement destination of the sample stage.

3. The focused ion beam apparatus according to claim 1,
wherein the control unit is configured to previously set the entire working region, and
wherein the control unit is configured to set a movement distance of the sample stage, based on the entire working region which has been previously set and the width representing the display size of the sample image displayed on the display unit.

4. The focused ion beam apparatus according to claim 1, wherein the control unit is configured to:
set a movement distance of the sample stage; and
detect the location of the reference mark on the sample image before the movement, based on the movement distance.

5. The focused ion beam apparatus according to claim 3, wherein the control unit is configured to form the reference mark based on the movement distance.

6. The focused ion beam apparatus according to claim 4, wherein the control unit is configured to form the reference mark based on the movement distance.

7. The focused ion beam apparatus according to claim 1, wherein after performing the working in the sample image after the movement of the sample stage, the control unit is configured to:
   set a new working area in the sample stage;
   form a new location detection mark at a location different from that of the reference mark in the sample image;
   extract each of feature amounts from the sample images before and after the forming of the location detection mark; and
   control an emission location of the focused ion beam to be emitted to the new working area so as to correct a location shift between the feature amounts.

8. A method of working a sample using a focused ion beam apparatus, the method comprising:
   generating a sample image including location detection marks formed on a sample, based on secondary charged particles generated from the sample by emission of a focused ion beam to the sample which is a working target;
   displaying the sample image;
   moving a sample stage on which the sample is placed; and
   in a case of performing working by emitting the focused ion beam to a working region of the sample that is beyond a display range of the displayed sample image,
   forming location detection marks on at least one of the sample and the sample image on the display unit;
   performing working of at least part of the working region of the sample by irradiating the sample with the ion beam on a first sample image while detecting a location of a first location detection mark formed at a processing starting point side and controlling an emission location of the focused ion beam based on the first location detection mark to correct a working location shift due to movement of the sample;
   detecting a location of any one of the location detection marks which is to be included in a second sample image after the movement of the sample stage as a reference mark, from the location detection marks included in the first sample image before the movement of the sample stage;
   switching the sample image from the first sample image which includes a processed working region to the second sample image which includes an unprocessed working region by moving the sample stage;
   performing working of the unprocessed working region by irradiating the sample with the ion beam on the second sample image while detecting a location of the reference mark in the sample image after the movement of the sample stage; and
   controlling an emission location of the focused ion beam based on the reference mark to correct a working location shift due to movement of the sample stage.

9. A non-transitory computer-readable medium having a computer program for focused ion beam working stored thereon and readable by a computer, the computer program, when executed by the computer, causes the computer to perform operations comprising:
   an image generation process of generating a sample image including location detection marks formed on a sample, based on secondary charged particles generated from the sample by emission of a focused ion beam to the sample which is a working target;
   displaying the sample image;
   moving a sample stage on which the sample is placed; and
   in a case of performing working by emitting the focused ion beam to a working region of the sample that is beyond a display range of the displayed sample image:
   forming location detection marks on at least one of the sample and the sample image on the display unit;
   performing working of at least part of the working region of the sample by irradiating the sample with the ion beam on a first sample image while detecting a location of a first location detection mark formed at a processing starting point side and controlling an emission location of the focused ion beam based on the first location detection mark to correct a working location shift due to movement of the sample;
   detecting a location of any one of the location detection marks, which is included in a second sample image after the movement of the sample stage as a reference mark, from the location detection marks included in the first sample image before the movement of the sample stage;
   performing working of the unprocessed working region by irradiating the sample with the ion beam on the second sample image while detecting a location of the reference mark in the sample image after the movement of the sample stage; and
   controlling an emission location of the focused ion beam based on the reference mark to correct a working location shift due to movement of the sample stage.

10. The focused ion beam apparatus according to claim 1, the control unit is configured to form the location detection marks on the sample.

11. The focused ion beam apparatus according to claim 1, wherein the first sample image is displayed with a first magnification, which is set to be a width representing the display size of the first sample image divided by a width of the ion beam.

12. The focused ion beam apparatus according to claim 11, wherein the control unit is configured to form location detection marks in response to an entire working region being set on a third sample image with a second magnification displaying the entire working region, the second magnification being smaller than the first magnification.

13. The focused ion beam apparatus according to claim 12, wherein the control unit is configured to, after forming the location detection marks on the third sample image, switch the sample image from the third sample image with the second magnification to the first sample image with the first magnification and to perform the working of at least part of the working region of the sample.

14. The method according to claim 8, wherein the first sample image is displayed with a first magnification, which is set to be a width representing the display size of the first sample image divided by a width of the ion beam.

15. The method according to claim 14, wherein the location detection marks are formed after an entire working region is set on a third sample image with a second magnification displaying the entire working region, the second magnification being smaller than the first magnification.

16. The method according to claim 15, wherein, after forming the location detection marks on the third sample image, switching the sample image from the third sample image with the second magnification to the first sample image with the first magnification and performing the working of at least part of the working region of the sample.

17. The non-transitory computer-readable medium according to claim 9, wherein the first sample image is displayed with a first magnification, which is set to be a width representing the display size of the first sample image divided by a width of the ion beam.

18. The non-transitory computer-readable medium according to claim 17, wherein the location detection marks are formed after an entire working region is set on a third sample image with a second magnification displaying the entire working region, the second magnification being smaller than the first magnification.

19. The non-transitory computer-readable medium according to claim 18, wherein, after forming the location detection marks on the third sample image, switching the sample image from the third sample image with the second magnification to the first sample image with the first magnification and performing the working of at least part of the working region of the sample.

* * * * *